United States Patent [19]

Ryan

[11] Patent Number: 5,078,690

[45] Date of Patent: Jan. 7, 1992

[54] HIGH PRESSURE SYRINGE

[75] Inventor: James P. Ryan, Amherst, N.H.

[73] Assignee: Accumed Systems, Incorporated, Southfield, Mich.

[21] Appl. No.: 464,966

[22] Filed: Jan. 11, 1990

[51] Int. Cl.[5] .............................................. A61M 5/00
[52] U.S. Cl. .................................... 604/187; 222/323
[58] Field of Search ...................... 604/187, 212, 218; 222/95, 323, 324, 369, 370

[56] References Cited

U.S. PATENT DOCUMENTS

| | | | |
|---|---|---|---|
| 1,039,591 | 9/1912 | Prideaux . | |
| 3,831,815 | 8/1974 | Glasgow | 222/95 |
| 4,014,331 | 3/1977 | Head | 128/224 |
| 4,581,021 | 4/1986 | Landau et al. | 604/212 |
| 4,594,073 | 6/1986 | Stine | 604/187 |
| 4,742,963 | 5/1988 | Marvaldi | 222/323 |
| 4,744,789 | 5/1988 | Johnson | 604/218 |

FOREIGN PATENT DOCUMENTS

| | | | |
|---|---|---|---|
| 3048761 | 7/1982 | Fed. Rep. of Germany | 604/187 |
| 2162426 | 2/1986 | United Kingdom | 604/187 |
| 2187962 | 9/1987 | United Kingdom | 604/187 |

OTHER PUBLICATIONS

Advertisement for Angioinject Syringe available from ACS.
Disclosure of Clear Shot Angio Plasti Inflation Device available from Mallinckrodt.
Disclosure of Biopsy Device available from Med-Tech Group.
Disclosure of Inflation Syringe available from USCI.
Disclosure of Dilation Balloon Inflation Pistol available from Cook.
Disclosure of Control EASE Syringe available from FMP.

Primary Examiner—C. Fred Rosenbaum
Assistant Examiner—Sharon Finkel
Attorney, Agent, or Firm—Hayes, Soloway, Hennessey & Hage

[57] ABSTRACT

A hand-held optimal injection high pressure syringe device, typically used for injecting viscous dye into a catheter or manifold. A pistol grip shape permits application of the full compressive force of the closing of the human hand. The syringe assembly is constructed of two major clear plastic sections plus a sealing tip attached to the injector end of the piston. The assembled syringe can be sterilized using standard procedures and disposed of following use. The simple design geometry permits use of efficient and low cost plastic injection molding techniques for manufacture.

12 Claims, 2 Drawing Sheets

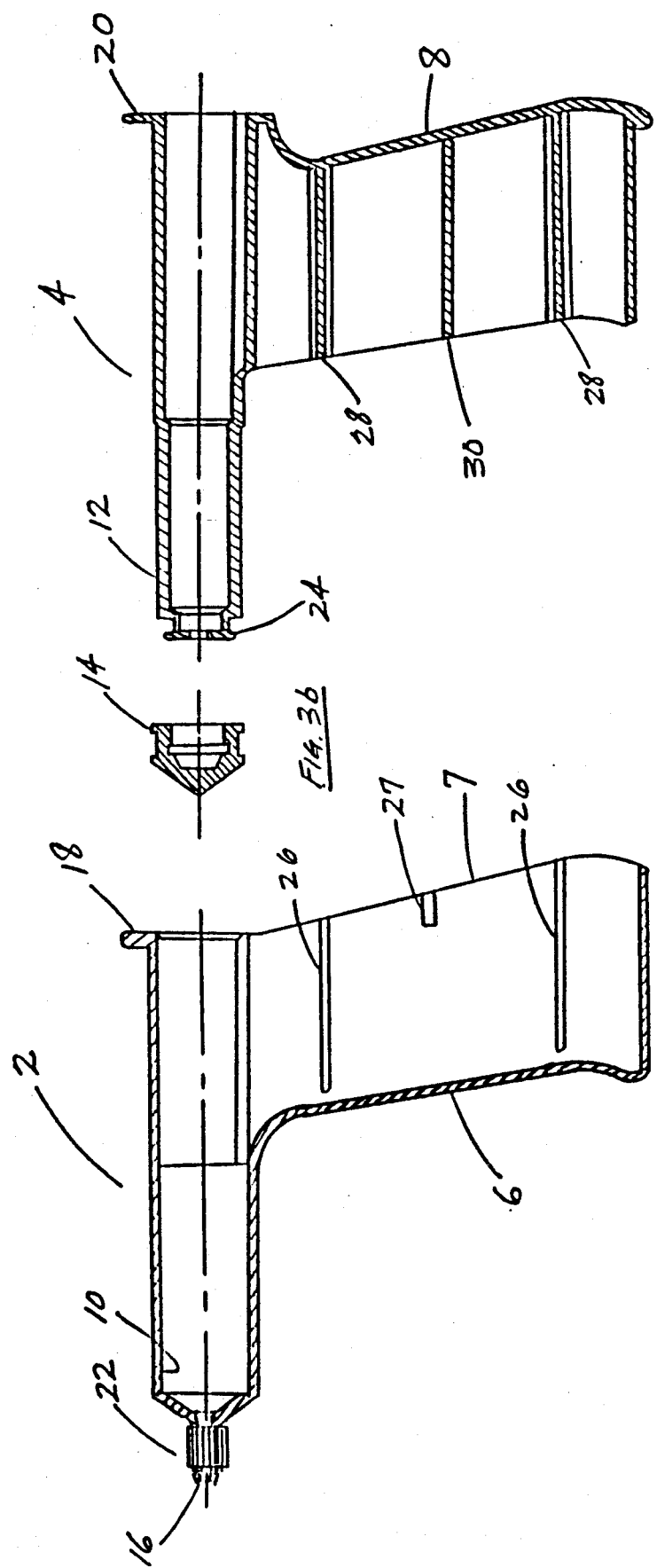

HIGH PRESSURE SYRINGE

BACKGROUND OF THE INVENTION

1. Field of Invention

The present invention is directed to syringes The invention has particular utility for injecting viscous materials into a manifold, needle, catheter or the like; for example, the very viscous dye required to visualize coronary anatomy in diagnosis and treatment of arterial diseases, and will be described in connection with such utility, although other utilities are contemplated.

2. Description of the Prior Art

Currently available syringes require the exertion of a tremendous amount of hand pressure, often resulting in suboptimal injections and hand fatigue. Most syringes used for this purpose involve two loops on opposite sides of the syringe for the first and second fingers and a plunger which either fits in the palm of the hand or is operated by the thumb. Such syringes are marketed by NAMIC, MERIT, Statco, Freund and other medical device manufacturers A syringe produced by ACS, a division of Eli Lilly, is advertised as being patented.

SUMMARY OF THE INVENTION

The present invention is directed to a hand-held syringe which is disposable, inexpensive, easy to use and capable of generating the high pressure necessary to inject a viscous liquid solution such as a contrast fluid under carefully controlled conditions. It is so constructed that it basically is a two piece construction and is designed so that it can be readily sterilized and takes advantage of the full strength of the human hand.

DETAILED DESCRIPTION OF THE INVENTION

The invention comprises a molded plastic structure having two basic portions. The first portion is an outer cylindrical body having an internal cylinder which communicates with a front liquid outlet for high pressure viscous fluid. The outer body portion has an integral hollow handle depending therefrom, the hollow handle being open to the rear. The second major portion is an inner piston portion which fits within the cylinder and carries means for sealing the piston and the cylinder against leakage of high pressure fluid. The piston also has a handle depending therefrom. The inner handle is arranged for free movement within the hollow handle with a portion of the inner handle extending through the opening in the rear of the hollow handle. With the above construction, when the inner handle and the hollow handle are squeezed together, the piston is moved forward in the cylinder to create a high pressure in the viscous fluid in the cylinder to force the fluid into an injection system, comprised of a manifold, catheter or the like.

In order to more fully understand the present invention, reference should be made to the following detailed description in connection with the accompanying drawings.

BRIEF DESCRIPTION OF THE DRAWINGS

FIG. 3a is a syringe outer housing section view.

FIG. 3b is a syringe piston seal section view.

FIG. 3c is a syringe inner housing section view.

DESCRIPTION OF THE PREFERRED EMBODIMENT

Figure 1:
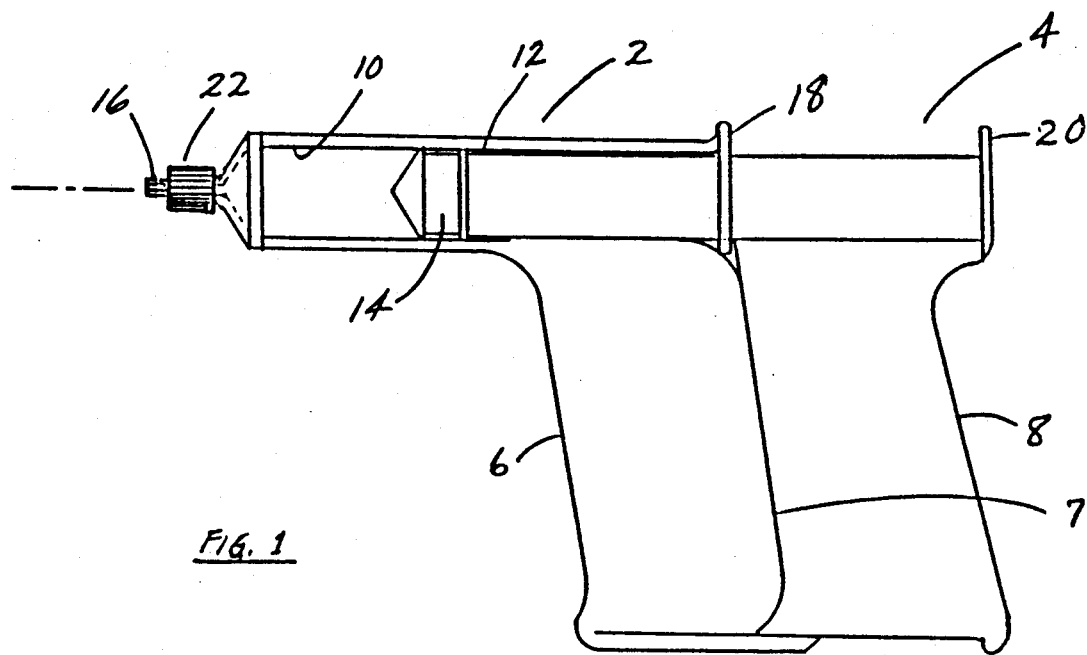
FIG. 1 is a side elevation view of high pressure syringe unit made in accordance with the present invention with inner housing extended.
Figure 2:
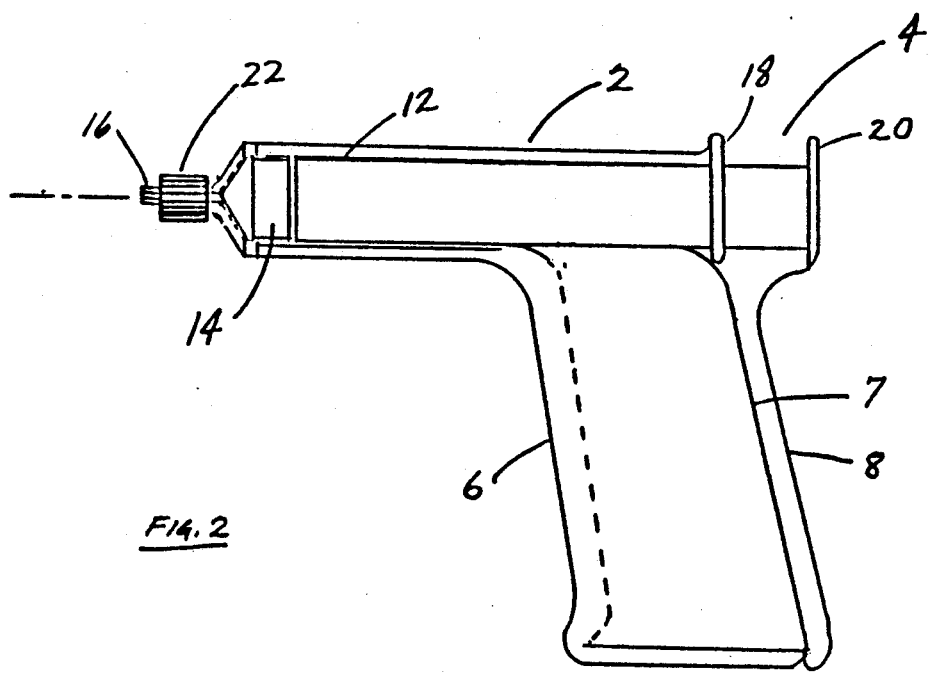
FIG. 2 is a high pressure syringe unit with inner housing compound.

Referring now to FIGS. 1 and 2, which are assembly drawings, the syringe comprises an outer housing portion generally indicated at 2, and an inner portion generally indicated at 4. The outer portion 2 preferably is formed of an optically transparent material, and has a downwardly extending finger grip handle 6 which is shown to be open at the rear 7. The inner housing has a downwardly extending inner handle 8 which fits within the opening 7. The upper part of the outer housing 2 defines an inner cylinder 10 in which a piston 12, carried by the inner housing 4, can fit. Outer housing portion 2 and inner portion 4 each preferrably comprise unitary molded parts formed of a medically approved materials such as polycarbonate or polypropylene. A resiliently deformable sealing tip 14, formed of a medical grade rubber, elastomer or the like, or an O-ring is carried on the forward end 24 of piston 12 and provides a high pressure seal between the piston 12 and the inner cylinder 10. A fluid feed opening 16 is provided in outer housing 2 to permit egress of the high pressure viscous liquid into a suitably attached catheter, manifold, needle or the like.

The catheter or other injection system device is attached with a female coupling known in the trade as a LUER-LOK to the outer housing male LUER-LOK tip 22. An alternative embodiment utilizes a captive and rotatable female threaded fitting with an O-ring seal affixed to the syringe tip 22. Both embodiments incorporate rotatable couplings that are snapped together.

In FIGS. 3a, b and c the various parts are shown in an exploded view wherein the simplicity of the various pieces is well illustrated. Both the inner and the outer pieces include flanges 18 and 20 at the rear of the cylinder and piston, respectively which aids in the withdrawal of the piston 12 to permit filling of the cylinder 10 with the requisite amount of viscous liquid from a suitable supply therefore, either before or after the device is connected to a manifold or inserted catheter.

In order to maintain relative alignment of the inner and outer housings during translation of the piston in the cylinder, the inner and outer housings preferably are provided with integrally formed cooperating tongue and grooves 26 and 28 respectively. A structural support rib 30 is provided within the otherwise hollow inner member handle 8. A locking tab 27 is provided within the outer member handle 6, its purpose being to prevent full withdrawal of the inner member handle 8 after the two members have been assembled.

Suitable volumetric indicia may be provided on either the outer or inner housing to indicate the amount of viscous fluid drawn into the syringe. When the syringe contains the requisite amount of fluid, pressure on the fluid is created by squeezing the inner handle 8 into the outer hollow handle 6 to provide full hand pressure to the viscous liquid. This will provide a more than adequate force to inject the viscous contrast dye into the injection system and into the coronary artery or other vessel.

Various changes may be made in the foregoing without departing from the spirit and scope of the invention. For example, while the piston and cylinder have been shown as unitary molded parts, the piston and/or cylinder both may be formed of a plurality of parts which may be joined together, for example, by welding. Still other changes will be obvious to one skilled in the art.

I claim:

1. A fluid injection syringe comprising a first outer cylindrical body portion having an internal cylinder communicating with a front outlet for high pressure viscous fluid, an integral hollow handle depending from the outer cylindrical body portion, said hollow handle being open to the rear, a second inner piston portion within said cylinder with means sealing said piston and cylinder against leakage of fluid, said piston having an inner handle depending therefrom, said inner handle being arranged for free movement within said hollow handle, a portion of the inner handle extending through the opening in the rear of the hollow handle, whereby, when the inner handle and the hollow handle are squeezed together, the piston is moved forward in the cylinder to create a high pressure in any fluid in the cylinder to force the fluid through the outlet, and at least one pair of cooperating tongue and groove surfaces in the space between said inner handle and said hollow handle for maintaining alignment of the piston portion within the outer cylindrical body while translating the piston length.

2. An injection syringe for rapidly injecting a viscous fluid into a catheter inserted in a patient to be treated, said syringe comprising a molded plastic structure including two portions, a first outer cylindrical body portion having an internal cylinder communicating with a front outlet for high pressure viscous fluid, an integral hollow handle depending from the outer cylindrical body portion, said hollow handle being open to the rear and having an upper outer cylindrical portion having forward a substantially complete cylindrical wall and a rear portion which is open at the bottom to the hollow handle, a second inner piston portion within said cylinder with means sealing said piston and cylinder against leakage of high pressure viscous fluid, the upper cylindrical inner portion having a forward piston and a rear portion closing said rear portion of the outer rear cylindrical portion and having a unitary relatively thin handle, said thin handle being arranged for free movement, with travel controlled by a locking tab means, preventing said thin handle from being completely withdrawn from within said hollow handle, a portion of the thin handle extending through the opening in the rear of the hollow handle whereby when the thin handle and the hollow handle are squeezed together the piston is moved forward in the cylinder to create a high pressure in the fluid in the cylinder to force the fluid into an injection system, and at least one pair of cooperating tongue and groove surfaces in the space between the thin handle and the hollow handle for maintaining alignment of the piston portion within the outer cylindrical body portion while translating the piston length.

3. A high pressure syringe apparatus, comprising, in combination:

(a) a piston slidably mounted within a cylinder;

(b) means for slidably sealing the piston to the wall of the cylinder;

(c) a pistol grip handle comprising inner and outer housing members attached respectively to said piston and cylinder;

(d) at least one pair of cooperating tongue and groove surfaces in the space between the inner and outer housing handle members for maintaining alignment of the piston within the cylinder when translating the piston length;

(e) means on the piston for aiding withdrawal of the piston from cylinder to fill the syringe with an injectable medium;

(f) indicia means for indicating the volume of fluid space in the cylinder; and p1 (g) a locking tab for restraining said piston from being fully removed from within said cylinder once assembled.

4. A high pressure syringe apparatus of claim 3, wherein the cylinder comprises a one piece molded member having an integral pistol grip.

5. A high pressure syringe apparatus of claim 3, wherein the piston comprises a one piece molded member having an integral pistol grip.

6. A high pressure syringe apparatus of claim 3, wherein the means for slidably sealing said piston to said cylinder comprises at least one seal member located in the clearance space between said piston and cylinder.

7. A high pressure syringe apparatus of claim 3, wherein said pistol grip handle comprises a forward outer housing member with a gripping surface of size to accommodate multiple human fingers to wrap around and squeeze; and a rearward inner housing member with a compression surface of size to accommodate the palm and thumb of a human hand.

8. A high pressure syringe apparatus of claim 3, wherein the means for aiding withdrawal of said piston from said cylinder comprises a flange located on each of said inner and outer housings, suitable for gripping with fingers of opposing hands whereby to at least partially withdraw said piston and draw an injectable fluid into said cylinder.

9. A high pressure syringe apparatus of claim 3, and including means for coupling said syringe to an injection system, said means for coupling comprising a suitably dimensioned mating surface for connection to a connectible complementary self-seal fitting on said injection system.

10. A high pressure syringe apparatus of claim 3, and including means for coupling said syringe to an injection system, said means for coupling comprising a captive and rotatable female threaded fitting, suitable to form a sealed connection of said syringe to a connectible complementary fitting on said injection system.

11. A high pressure syringe apparatus of claim 3, wherein the indicia means for indicating the volume of said fluid space in said cylinder is comprised of (a) a suitable marked graduated scale on the outer housing cylinder; and (b) a witness mark on the piston, located adjacent said scale for observing said cylinder volume.

12. A high pressure syringe apparatus of claim 3, wherein the indicia means for indicating the volume of said fluid space in said cylinder is comprised of (a) a suitable marked graduated scale on the inner housing piston member; and (b) a witness mark on the outer housing cylinder located adjacent said scale for observing said cylinder volume.

* * * * *

UNITED STATES PATENT AND TRADEMARK OFFICE
CERTIFICATE OF CORRECTION

PATENT NO.  : 5,078,690
DATED       : January 7, 1992
INVENTOR(S) : James P. RYAN It is certified that error appears in the above-identified patent and that said Letters Patent is hereby corrected as shown below:

"Claim 3, Col. 4, Line 13, "pl" should be deleted.

Signed and Sealed this

First Day of June, 1993

Attest:

MICHAEL K. KIRK

*Attesting Officer*      Acting Commissioner of Patents and Trademarks